United States Patent [19]

Crossley

[11] 4,132,798
[45] Jan. 2, 1979

[54] PHARMACEUTICAL COMPOSITIONS CONTAINING 4-AMIDO-THIAZOLES

[75] Inventor: Roger Crossley, Reading, England

[73] Assignee: John Wyeth & Brother Ltd., Taplow, England

[21] Appl. No.: 887,159

[22] Filed: Mar. 16, 1978

[30] Foreign Application Priority Data

Mar. 29, 1977 [GB] United Kingdom ............ 13233/77

[51] Int. Cl.$^2$ .......................................... A61K 31/425
[52] U.S. Cl. ................................. 424/270; 424/127; 424/131; 424/155; 424/156; 424/157
[58] Field of Search .......................................... 424/270

[56] References Cited

PUBLICATIONS

Monetshefte fur Chemie, 1027–1032 (1975).
J. Chem. Soc., C, 1357–1360 (1966).
Bull. Chem. Soc. Japan, 38, 1816–1820 (1965).
Proc. Indian Acad. Sci., 1945, 22A, 359–361.

Primary Examiner—Frederick E. Waddell
Attorney, Agent, or Firm—Arthur E. Wilfond

[57] ABSTRACT

The invention relates to pharmaceutical compositions for use in treating ulcers or hypersecretion comprising a compound of formula I

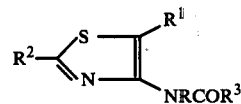

wherein R is hydrogen, alkyl of 1 to 6 carbon atoms, or $COR^3$ where $R^3$ is hydrogen, alkyl of 1 to 5 carbon atoms, alkenyl of 2 to 5 carbon atoms, alkynyl of 2 to 5 carbon atoms or cycloalkyl of 3 to 5 carbon atoms; $R^1$ is hydrogen or alkyl of 1 to 6 carbon atoms, $R^2$ is alkyl of 1 to 6 carbon atoms or phenyl optionally substituted by halogen, alkyl of 1 to 6 carbon atoms or alkoxy of 1 to 6 carbon atoms, and $R^3$ is as defined above, and a pharmaceutically acceptable carrier.

15 Claims, No Drawings

PHARMACEUTICAL COMPOSITIONS CONTAINING 4-AMIDO-THIAZOLES

This invention relates to novel pharmaceutical compositions containing compounds having anti-secretory activity, to methods of treating ulcers or hypersecretion in mammals using such compounds or compositions, and to novel compounds used in such compositions.

In Monatshefte fur Chemie 106, 1027–1032 (1975) Benko and Rotaru disclose the preparation of some 4-acetamido-thiazoles having 2-methyl, 2-phenyl, 2-m-tolyl and 2-p-tolyl substituents. 2-phenyl-4-acetamido-thiazole is disclosed in J. Chem. Soc, C, 1966(6) and in Bull Chem. Soc. Japan Vol. 38 No. 11 1965 1816–1820. No pharmaceutical applications of any of these compounds have been reported so far as I am aware. I have now surprisingly found that these 4-acetamido-thiazoles form part of a class of compounds having anti-secretory activity.

Anti-secretory activity was determined by the test of H. Shay, D. Sun and H. Greenstein, Gastroenterology, 1954, 26, 903-13. Compounds which possess this activity are considered to be anti-ulcer agents which can be used for the treatment of ulcers or hypersecretion in mammals.

The present invention provides a pharmaceutical composition for use in treating ulcers or hypersecretion comprising a compound of formula I

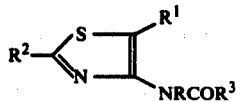

wherein R represents hydrogen, alkyl of 1 to 6 carbon atoms or $COR^3$ wherein $R^3$ is hydrogen, alkyl of 1–5 carbon atoms, alkenyl of 2 to 5 carbon atoms, alkynyl of 2 to 5 carbon atoms, cycloalkyl of 3 to 5 carbon atoms, $R^1$ is hydrogen or alkyl of 1 to 6 carbon atoms, and $R^2$ is alkyl of 1 to 6 carbon atoms or a phenyl radical which is unsubstituted or substituted by halogen, alkyl of 1 to 6 carbon atoms or alkoxy of 1 to 6 carbon atoms, and a pharmaceutical carrier.

In the compounds of formula I, Examples of $R^3$ are for the alkyl group: methyl, ethyl, n-propyl, isopropyl or n-butyl; for alkenyl group: vinyl, prop-1-enyl, but-1-enyl, but-2-enyl; for the alkynyl group: ethynyl, prop-2-ynyl, but2-ynyl; and for the cycloalkyl group: cyclopropyl, cyclobutyl and cyclopentyl.

The term "alkyl group of 1 to 6 carbon atoms" contemplates both straight and branched chains; e.g. methyl, ethyl, n-propyl iso-propyl, n-butyl, s-butyl, t-butyl, n-pentyl, or n-hexyl. Preferably the alkyl group contains 1 to 4 carbons.

$R^1$ when alkyl of 1-6 carbon atoms may be any of the lower alkyl radicals discussed above but is preferably methyl or ethyl.

Preferably R is hydrogen. Preferably $R^3$ is methyl. Preferably $R^1$ is hydrogen.

$R^2$ when alkyl of 1-6 carbon atoms may be any of the lower alkyl radicals discussed above but is preferably methyl. Further examples of $R^2$ are phenyl, phenyl substituted by lower alkyl selected from methyl, ethyl, n-propyl and isopropyl; phenyl substituted by lower alkoxy selected from methoxy, ethoxy, n-propoxy and isopropoxy and phenyl substituted by halogen selected from fluorine, chlorine and bromine.

The compounds of formula I are anti-ulcer agents which possess activity in the above mentioned test of Shay et al.

The invention includes a process for preparing a pharmaceutical composition which comprises bringing an effective amount of a compound of formula I into association with a pharmaceutically acceptable carrier.

Preferably the pharmaceutical composition is in unit dosage form, e.g. as tablets or capsules.

For the pharmaceutical carrier any suitable carrier known in the art can be used to prepare the pharmaceutical compositions. In such a composition, the carrier may be a solid, liquid or mixture of a solid and a liquid.

Solid form compositions include powders, tablets and capsules. A solid carrier can be one or more substances which may also act as flavouring agents, lubricants, solubilisers, suspending agents, binders or tablet disintegating agents; it can also be an encapsulating material. In powders the carrier is a finely divided solid which is in admixtuie with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "compositions" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 mg. or less to 500 mg. or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The preferred compounds of formula I used in the pharmaceutical compositions of the invention are those in which $R^2$ is methyl or phenyl, R is hydrogen, $R^3$ is methyl and $R^1$ is hydrogen.

Compounds of formula I wherein R is hydrogen may be prepared by a process which comprises carrying out a Beckmann rearrangement of an oxime of formula (II).

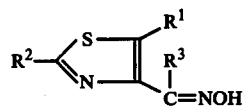

wherein $R^1$ and $R^2$ are as defined in connection with formula I and $R^3$ is as defined in connection with formula I, except hydrogen.

The rearrangement is carried out under standard conditions for the Beckmann rearrangement, e.g. phosphorus pentachloride in ether.

The starting compounds of formula (II) may be prepared by known methods, e.g. by reaction of a thioamide (III) with an oxime (IV).

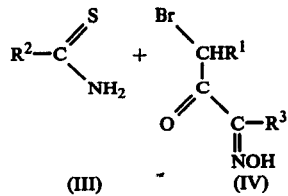

In formulae (III) and (IV) $R^1$ and $R^2$ are as defined in connection with formula I and $R^3$ is as defined in connection with formula I except hydrogen.

Alternatively a compound of formula (V)

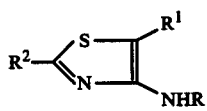

where $R^2$, $R^1$ and R are as defined in connection with formula I, may be acylated. This method may be used to prepare both mono and diacyl-amino compounds.

Standard acylating agents capable of introducing the group $R^3CO$ may be used e.g. the acid chloride $R^3COCl$, acid anhydride

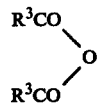

or mixed anhydride

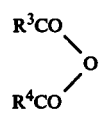

where $R^3$ is as defined above and $R^4$ is a different $R^3$ group.

When the group $R^3CO$ is formyl, formylation may be achieved by use of the mixed anhydride of formic acid and acetic acid which can be produced from formic acid in acetic anhydride.

When the group $R^3$ is alkyl carrying a substituent functional group then one such group may be converted to another by standard methods.

Starting compounds of formula (V) where R is $COR^3$ may be prepared by acylation of the corresponding compounds where R is hydrogen.

Compounds of formula I may also be prepared by Curtius rearrangement of a thiazole ester of formula (VI)

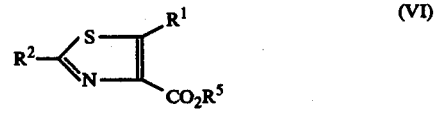

where $R^1$ and $R^2$ are as defined in connection with formula I and $R^5$ is lower alkyl.

The ester of formula (VI) is treated with hydrazine to give the hydrazide of formula (VII)

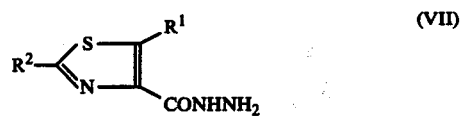

followed by nitrous acid to give the carbonyl azide of formula (VIII)

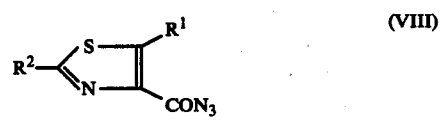

The azide (VIII) may then be rearranged with an acid anhydride or mixed anhydride to give a compound of formula I wherein R is hydrogen and $R^3$ is as defined in connection with formula I. Thus an acid of formula (VIII) wherein $R^1$ and $R^2$ are as defined in connection with formula I may be rearranged by treatment with an acid anhydride of formula

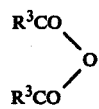

or a mixed anhydride of formula

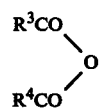

wherein $R^3$ is as defined in connection with formula I and $R^4$ is a different $R^3$ group.

When a compound of formula I is prepared wherein R is hydrogen, this may be alkylated, for example by treatment with an alkali metal hydride (e.g. sodium hydride) or equivalent base and an alkylating agent (such as a di(lower-alkyl)sulphate, alkyl tosylate or a lower alkyl halide) to give a compound of formula I wherein R is lower alkyl.

Pharmacological Test Results

When tested orally in rats, representative compounds, namely 4-acetamido-2-methyl-thiazole and 4-acetamido-2-phenylthiazole, both showed good antisecretory activity in the test of Shay et al at 30 mpk as shown below.

| Compound | mpk ID | Vol | Conc | Anti-secretory (Shay et al) Free H$^+$ | Total H$^+$ |
|---|---|---|---|---|---|
| 4-Acetamido-2-methylthiazole | 30 | −71% | Insuff. NS | gastric −36 | juice for titration −35 |
| | 10 | −32 | | | |
| 4-Acetamido-2-phenylthiazole | 30 | −83 | −47 | −88 | −83 |
| | 10 | −39 | −19 | −56 | −45 |

NS = Not Significant

The invention also includes a method of treating ulcers or hypersecretion in an afflicted mammal which method comprises administering to said mammal an effective amount of a compound of formula I as defined above. The dose will be varied according to the activity of the compound. For a compound such as 4-acetamido-2-phenylthiazole the amount of active ingredient may be from 10 to 100 mg/kg.

Preferably the compound used is 4-acetamido-2-methylthiazole or 4-acetamido-2-phenylthiazole.

The invention also provides novel compounds falling within the scope of the compounds of formula I defined above. These compounds have the formula

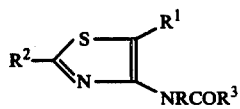

(Ia)

wherein R, R$^1$, R$^2$ and R$^3$ are as hereinbefore defined with the provisos that (i) when R$^2$ is methyl, phenyl, m-tolyl or p-tolyl, R is hydrogen, R$^3$ is methyl then R$^1$ is lower alkyl and (ii) when R$^2$ is phenyl and R is COR$^3$ then R$^3$ is other than methyl.

The following examples illustrate pharmaceutical compositions in accordance with the invention.

EXAMPLE A

| Suspension | % w/v |
|---|---|
| Aluminium hydroxide gel B.P.5% Al$_2$O$_3$ | 80%=4% Al$_2$O$_3$ |
| Magnesia Magma 12% w/v MgO | 10% |
| 4-acetamido-2-methylthiazole | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof. 60 O.P. represents 91% w/v Ethanol/Water.

The above suspension is prepared by the following procedure. Add to the Alumina gel Magnesia Magma followed by the thiazole dispersed in glycerin, the peppermint oil dissolved in alcohol, the saccharin sodium dissolved in water, and the p-hydroxybenzoates dissolved in water. Make up to volume of water and stir well. Dose: 5 ml. t.d.s.

EXAMPLE B

| Antacid Tablet (chewable) | |
|---|---|
| Saccharin | 1.0 mg. |
| Hydrated alumina sucrose powder | 750.0 mg. |
| 4-acetamido-2-phenyl-thiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE C

| Anti-ulcer tablet (without antacid) | mg/tablet |
|---|---|
| 4-acetamido-2-phenyl-thiazole | 100 mg. |
| Celutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallised.

Further pharmaceutical compositions may be prepared by replacing 4-acetamido-2-methylthiazole or 4-acetamido-2-phenylthiazole in any of Examples A to C with another thiazole of the invention, e.g. one of the thiazole of Examples 4-9 below.

The compounds employed in the invention and processes for preparing them are further illustrated by the following Examples.

EXAMPLE 1

4-Acetamido-2-phenyl-thiazole

A suspension of 4-(1-oximinoethyl)-2-phenylthiazole (6 g.) and phosphorus pentachloride (18 g.) in diethyl ether (1.5 liters) was stirred for 14 days with exclusion of moisture at ambient temperature. The diethyl ether was removed under reduced pressure and the residue suspended in water (200 ml.). The suspension was basified (Na$_2$CO$_3$) and the product removed by filtration and air dried. The resulting solid was extracted with chloroform and the chloroform solution evaporated under reduced pressure. The residue was recrystallised from benzene to give the title compound (200 mg.) Mpt: 165° C.

(Found: C, 60.2; H, 4.7; N, 12.4%; C$_{11}$H$_{10}$N$_2$OS requires: C, 60.5; H, 4.6; N, 12.8%).

EXAMPLE 2

4-Acetamido-2-phenylthiazole (a) A suspension of 2-phenylthiazole-4-carbohydrazide (17 g.) in water (100 ml.) was treated with 12N hydrochloric acid (20 ml.), followed by a solution of sodium nitrite (5.85 g.) in water (20 ml.) with external cooling via an ice bath. The reaction mixture was stirred 30 minutes and the product azide removed by filtration and washed with water.

(b) After air drying, the azide (17 g.) was suspended in a mixture of acetic anhydride (120 ml.) and acetic acid (30 ml.) and heated 30 minutes on a steam bath. The reaction mixture was cooled to room temperature and poured onto 20% aqueous sodium acetate (1 liter). The product was removed by filtration, washed with water and air dried. Recrystallisation from benzene gave the title compound (6 g.) Mpt. 167° C.

(Found: C, 60.9; H, 4.7; N, 12.9%; $C_{10}H_{10}N_2OS$ requires: C, 60.5; H, 4.6; N, 12.8%)

IR and n.m.r. spectra identical to authentic material.

EXAMPLE 3

4-Acetamido-2-methylthiazole

A mixture of 2-methyl-4-(1-oximinoethyl)thiazole (6 g.) and phosphorus pentachloride (18 g.) was suspended in diethyl ether (1.51 g.) and the mixture stirred at ambient temperature in a sealed flask for 14 days.

The solvent was removed under reduced pressure, the residue dissolved in water (200 ml.) and basified with $Na_2CO_3$ (pH9). The solution was filtered and the filtrate extracted with diethyl ether (3 × 200 ml.). The combined organic layers were dried ($MgSO_4$) and the solvent evaporated. The residue was extracted with hot hexane (3 × 50 ml.) the hot extracts were cooled and the product removed by filtration. Recrystallisation from hexane gave the title compound (1 g.) Mpt. 102° C.

(Found: C, 46.3; H, 5.1; N, 18.0%; $C_6H_8N_2OS$ requires: C, 46.1; H, 5.2; N, 17.9%).

EXAMPLE 4

4-Acetamido-2-ethylthiazole

Using a procedure analogous to Example 2, 2-ethylthiazole-4-carbohydrazide is treated with 12 N hydrochloric acid and a solution of sodium nitrite in water to give the corresponding azide, which compound is reacted with acetic anhydride/acetic acid to give the title compound.

EXAMPLE 5

4-Acetamido-2-(4'-chlorophenyl)thiazole

Using a procedure analogous to Example 2, 2-(4'-chlorophenyl)thiazole-4-carbohydrazide is treated with 12N hydrochloric acid and a solution of sodium nitrite in water to give the corresponding azide, which compound is reacted with acetic anhydride/acetic acid to give the title compound.

EXAMPLE 6

4-Acetamido-2,5-dimethylthiazole

Using a procedure analogous to Example 2, 2,5-dimethylthiazole-4-carbohydrazide is treated with 12N hydrochloric acid and a solution of sodium nitrite in water to give the corresponding azide, which compound is reacted with acetic anhydride/acetic acid to give the title compound.

EXAMPLE 7

4-Acetamido-5-methyl-2-phenylthiazole

Using a procedure analogous to Example 2, 5-methyl-2-phenylthiazole-4-carbohydrazide is treated with 12N hydrochloric acid and a solution of sodium nitrite in water to give the corresponding azide, which compound is reacted with acetic anhydride/acetic acid to give the title compound.

EXAMPLE 8

4-(N-Acetyl-N-methylamino)-2-phenylthiazole

A mixture of 4-acetamido-2-phenylthiazole, prepared according to Example 1, and methyl tosylate in acetonitrile may be treated with sodium hydride to give the title compound.

EXAMPLE 9

4-Acrylamino-2-methylthiazole

4-Amino-2-methylthiazole (prepared by hydrolysing 4-acetamido-2-methylthiazole) is treated with acryloylchloride to give the title compound.

I claim:

1. A pharmaceutical composition for use in treating ulcers or hypersecretion comprising an effective amount of a compound of formula I

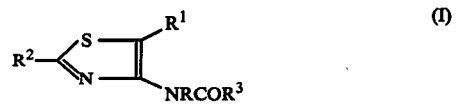

wherein R is hydrogen, alkyl of 1 to 6 carbon atoms, or $COR^3$ where $R^3$ is hydrogen, alkyl of 1 to 5 carbon atoms, alkenyl of 2 to 5 carbon atoms or cycloalkyl of 3 to 5 carbon atoms; $R^1$ is hydrogen or alkyl of 1 to 6 carbon atoms, $R^2$ is alkyl of 1 to 6 carbon atoms or phenyl optionally substituted by halogen, alkyl of 1 to 6 carbon atoms or alkoxy of 1 to 6 carbon atoms, and $R^3$ is as defined above, and a pharmaceutically acceptable carrier.

2. A pharmaceutical composition as claimed in claim 1, in unit dosage form.

3. A pharmaceutical composition as claimed in claim 2 in the form of a tablet or capsule.

4. A pharmaceutical composition as claimed in claim 1 wherein $R^1$ is hydrogen or alkyl of 1 to 6 carbon atoms, $R^3$ is alkyl of 1 to 6 carbon atoms, R is hydrogen or alkyl of 1 to 6 carbon atoms, $R^2$ is alkyl of 1 to 6 carbon atoms, phenyl or phenyl substituted by halogen, alkyl of 1 to 6 carbon atoms or alkoxy of 1 to 6 carbon atoms.

5. A pharmaceutical composition as claimed in claim 1 in which the compound of formula I is 4-acetamido-2-methylthiazole.

6. A pharmaceutical composition as claimed in claim 1 in which the compound of formula I is 4-acetamido-2-phenylthiazole.

7. A pharmaceutical composition as claimed in claim 1 in which the compound of formula I is 4-acetamido-2-ethylthiazole.

8. A pharmaceutical composition as claimed in claim 1 in which the compound of formula I is 4-acetamido-2-(4'-chlorophenyl)thiazole.

9. A pharmaceutical composition as claimed in claim 1 in which the compound of formula I is 4-acetamido-2,5-dimethylthiazole.

10. A pharmaceutical composition as claimed in claim 1 in which the compound of formula I is 4-acetamido-5-methyl-2-phenylthiazole.

11. A pharmaceutical composition as claimed in claim 1 in which the compound of formula I is 4-(N-acetyl-N-methylamino)-2-phenylthiazole.

12. A pharmaceutical composition as claimed in claim 1 in which the compound of formula I is 4-acrylamido-2-methylthiazole.

13. A pharmaceutical composition as claimed in claim 1 which includes an antacid ingredient.

14. A method of treating ulcers or hypersecretaion in an afflicted animal which method comprises administering to said mammal an effective amount of a compound of formula I as defined in claim 1.

15. A method as claimed in claim 14 wherein the compound of formula I is 4-acetamido-2-phenylthiazole or 4-acetamido-2-methylthiazole.

* * * * *